United States Patent
Bokrantz

(10) Patent No.: US 10,864,382 B2
(45) Date of Patent: Dec. 15, 2020

(54) SYSTEM AND METHOD FOR RADIATION THERAPY TREATMENT PLANNING

(71) Applicant: RaySearch Laboratories AB, Stockholm (SE)

(72) Inventor: Rasmus Bokrantz, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 246 days.

(21) Appl. No.: 15/959,470

(22) Filed: Apr. 23, 2018

(65) Prior Publication Data

US 2018/0304097 A1 Oct. 25, 2018

(30) Foreign Application Priority Data

Apr. 24, 2017 (EP) ..................................... 17167731

(51) Int. Cl.
| | |
|---|---|
| *A61N 5/10* | (2006.01) |
| *G06N 99/00* | (2019.01) |
| *G06N 5/02* | (2006.01) |
| *G16H 20/40* | (2018.01) |
| *G06N 20/00* | (2019.01) |
| *G06F 16/903* | (2019.01) |
| *G16H 50/70* | (2018.01) |
| *G16H 30/40* | (2018.01) |

(52) U.S. Cl.
CPC ......... *A61N 5/1031* (2013.01); *A61N 5/1039* (2013.01); *G06F 16/90335* (2019.01); *G06N 5/022* (2013.01); *G06N 20/00* (2019.01); *G16H 20/40* (2018.01); *G16H 30/40* (2018.01); *G16H 50/70* (2018.01); *A61N 2005/1041* (2013.01)

(58) Field of Classification Search
CPC ................ A61N 5/1031; A61N 5/1039; A61N 2005/1041; G16H 20/40; G16H 50/70; G16H 30/40; G06N 5/022; G06N 20/00; G06F 16/90335

See application file for complete search history.

(56) References Cited

U.S. PATENT DOCUMENTS

| | | | |
|---|---|---|---|
| 2011/0153547 A1* | 6/2011 | McNutt | G06F 19/3481 706/54 |
| 2014/0350863 A1 | 11/2014 | Hartman et al. | |
| 2015/0095043 A1* | 4/2015 | Cordero Marcos | G16H 50/70 705/2 |
| 2015/0095044 A1* | 4/2015 | Hartman | A61N 5/103 705/2 |

* cited by examiner

*Primary Examiner* — Christine H Matthews
*Assistant Examiner* — Joshua Daryl D Lannu
(74) *Attorney, Agent, or Firm* — Faegre Drinker Biddle & Reath LLP

(57) ABSTRACT

Radiation therapy treatment planning methods facilitate predicting achievable dose distributions by training a prediction model for clinical DVH curves based on simplified DVH curves obtained using standardized methods. Machine learning applied on pairs of clinical and simplified DVH curves enables predicting actual clinical DVH curves based on simplified DVH curves.

16 Claims, 1 Drawing Sheet

SYSTEM AND METHOD FOR RADIATION THERAPY TREATMENT PLANNING

RELATED APPLICATION DATA

This application claims priority under 35 U.S.C. § 119 and/or § 365 to European Application No. EP17167731 filed Apr. 24, 2017, the entire contents of which is incorporated herein by reference.

TECHNICAL FIELD

The present invention relates to a system, a method and a computer program product for automatic planning of radiation therapy treatment plans.

BACKGROUND

Radiation therapy treatment planning is generally performed on one or more computed tomography (CT) or other suitable images of a patient and involves both manual and automated steps. There is a desire to perform as much as possible of the treatment planning using automatic steps, because manual handling is time-consuming and constitutes a source for human error and inconsistencies between different operators. When preparing a treatment plan for a patient, it is advantageous to have access to a prediction of achievable dose metrics for the patient. Especially for new patients, it is useful to base such a prediction of previously treated patients. Such a prediction can be used as a reference that guides the operator during manual treatment planning, or used as input to an automated treatment plan generation method that recreates the predicted metrics to the largest possible extent. Calculation of an accurate prediction of achievable dose metrics for a new patient based on previously treated patients is a challenging problem.

The images used for treatment planning are augmented with structure sets, each structure in a structure set defining a region of interest, such as an organ, a target volume, or a help region such as a geometric margin around an organ or target. The structure set may be generated by manual contouring of the image slices of the planning images, or by automated segmentation methods that fit organ models from anatomical atlases to the planning image.

Dose Volume Histograms (DVH) are diagrams commonly used for radiation therapy planning, relating radiation dose to cumulative structure volume to determine the total dose coverage of a particular structure of a structure set. In automated radiation therapy treatment planning, it would be useful to be able to predict achievable DVH values for a current patient, to ensure that planning is based on realistic goals. Some previous methods exist, which are based on analysis of patient geometry and selecting data from previous patients that have similar geometry to the current patient.

For example, US2014/0350863 A1 discloses a model for predicting DVH curves for organs at risk for a current patient, based on data from previous patients. The model is based on distance to target histograms (DTH) for previous patients, each such DTH histogram expressing the distance from a region or structure, such as an organ at risk, to a target structure. The DVH curves associated with the clinical dose distribution of the previously treated patients are also retrieved. A principal component analysis (PCA) is performed on the DTH and DVH curves, thereby extracting low-dimensional features that describe the relationship between DTH and DVH. Machine learning is then applied on the extracted features to train a regression model to predict DVH curves based on DTH curves. The regression model can, once trained, be used to obtain a prediction of achievable DVH curves for a new patient based on the patient's DTH curves.

Another model for predicting DVH information based on previous patient geometry data is disclosed in US 2011/0153547, which proposes to calculate DVH points for organs at risk based on overlap volume histograms (OVH). The OVH of a structure is a curve plot that gives the percentage of the volume of the structure that is within a specified distance to the target. These OVHs are used to identify earlier patients with a similar or more challenging geometry. For a given cumulative volume, a DVH point is obtained as the lowest dose that has been achieved for the earlier, more challenging or similar patients.

Both of these models have some drawbacks. They are based on modification of geometric distances to obtain a predictor for the achievable dose. This is difficult to achieve.

SUMMARY

It is an object to facilitate the prediction of achievable DVH curves for a particular patient.

An embodiment proposes a method for use in radiation therapy treatment planning, comprising:
a. obtaining a protocol plan, which has been created by applying a plan generation protocol to a set of patient data for a current patient, said set of patient data comprising at least one planning image;
b. calculating at least one protocol DVH curve, each protocol DVH curve relating a dose distribution for the protocol plan to a volume of a structure in a structure set associated with the at least one planning image;
c. obtaining estimated clinical DVH curves by sending the at least one protocol DVH curve as a query to a prediction model, the prediction model being arranged to determine estimated clinical DVH curves on the basis of protocol DVH curves for the current patient based on a relationship between protocol DVH curves and clinical DVH curves for a collection of previous patients;
d. using at least one of the estimated clinical DVH curves in treatment planning for the current patient.

An embodiment also proposes a method of training a prediction model for use in radiation therapy treatment planning, the prediction model being capable of creating an estimated clinical DVH curve based on a protocol DVH curve for a structure to an estimated clinical DVH curve for the structure. The training of the prediction model comprises the following steps:
e. obtaining a set of patient data for a previous patient, the set of patient data comprising at least one planning image and;
f. obtaining a plan generation protocol;
g. obtaining a protocol plan by applying the plan generation protocol to the set of patient data;
h. calculating at least one protocol DVH curve for the patient, each protocol DVH curve relating a dose distribution for the protocol plan of the previous patient to a volume of a structure in a structure set associated with the at least one planning image;
i. obtaining a clinical DVH curve associated with each protocol DVH curve, each clinical DVH curve relating a clinical dose distribution of the patient to the volume;

j. repeating steps e-i for each of a number of previous patients to obtain a number of pairs including a protocol DVH curve and an associated clinical DVH curve;
k. selecting a subset of the pairs of DVH curves;
l. defining a functional relationship between protocol DVH and estimated clinical DVH based on a relationship between each pair of protocol DVH curve and associated clinical DVH curve of a previous patient.

The method of training the prediction model is based on a collection of previously treated patients with associated clinical dose distributions. However, the method is based on analysis of dose distribution data instead of geometric data. Preferably, the execution of the plan generation protocol can be implemented in fully automated fashion.

According to an embodiment, the estimated clinical DVHs are calculated based on data from previous patients that have similar protocol DVHs, where the protocol DVHs of the previous patients are preferably generated using the same protocol as that used to generate the protocol DVH for the current patient and defined with respect to corresponding structure sets. This is in contrast to the prior art cited above, where the prediction of clinical DVHs is based on data from previous patients that have similar geometry.

Protocol dose is a more realistic predictor for an achievable dose than a simple geometric distance as is used in the prior art. Prediction of DVH curves based on information derived from dose distributions leads to simplified handling from several points of view compared to predictions based on geometric information. In particular, the following aspects, that are not reflected in geometric information such as DTH or OVH curves, are reflected in the protocol DVH curves and therefore need no special handling:
  the dose to the out-of-field parts of an organ at risk that are shielded by the jaws is zero (or small);
  the dose to a point in the patient volume from a given beam is dependent on the radiological depth of the point relative to the beam, the relationship decreases exponentially with increasing radiological depth for photon beams and the relationship increases up to a Bragg peak depth for charged particle beams, and then decreases to zero; and
  the dose to a point is not only dependent on the geometric distance to a target volume, but also on the target's prescription dose level. Therefore, it is not trivial to define predicted point doses for simultaneous integrated boost (SIB) treatments where multiple targets are treated concurrently to different dose prescriptions.

The use of a protocol dose distribution as the basis for the DVH prediction is directly applicable to SIB treatments as the protocol may be configured to generate the desired form of SIB treatments. Thereby, the property that the dose to a point in the patient volume in proximity of a low-dose target will be comparatively lower than for a similar point in proximity of a high-dose target is incorporated in the dose of the protocol plan, because the plan generation protocol is configured to generate the desired low dose for the low-dose target.

By similar reasoning, the use of protocol DVH as predictive metric also extends to multimodality treatments where beams using at least two different treatment modalities, such as photons and protons, are used. The plan generation protocol may, for this application, be configured to generate a multimodality treatment plan, the plan generation protocol preferably incorporating concurrent optimization of all radiation beams. Thereby, the calculated dose of the protocol plan to a point in the patient volume will reflect that the actual dose to the point depends on which modality the point primarily receives dose from. This information is not reflected in the geometric location of the point relative to a target or the union of a set of targets and therefore cannot be obtained with the prior art methods.

In each of the methods above, the plan generation protocol may involve analysis of the provided input data and monitoring of the progress of the protocol execution, as well as adaptation accordingly. A protocol may, for example, query a structure set against a template set of structures and then generate all structures in the template set that have not yet been defined. The plan generation protocol may similarly add beam definitions according to a set of template beams if no preselected beam configuration is present in the input patient data.

The tasks included in a plan generation protocol typically include one or more of the following:
  augmenting the structure sets with additional structures, either manually or by automatic image segmentation,
  selection of at least on treatment technique,
  definition of radiation beams, for each treatment technique if more than one has been selected,
  definition of calculation settings such as the dose grid resolution and tolerances,
  definition of tolerances such as a maximum number of beam segments and a maximum number of iterations during an optimization,
  definition of an optimization problem and/or optimization functions,
  optimizing a dose of the radiation beams with respect to an optimization problem,
  updating of the optimization functions based on assessment of a dose distribution,
  calculating the clinical dose distribution.

A functional relationship between protocol DVH and estimated clinical DVH may be used to estimate a clinical DVH based on a protocol DVH curve for a structure of a structure set associated with the at least one planning image. The functional relationship between protocol DVH and estimated clinical DVH preferably takes a protocol DVH curve for a structure of a structure set associated with the at least one planning image as argument and returns an estimated clinical DVH curve for the structure. The estimated clinical DVH curve may be described by a sequence of coordinates pairs (x, y), each coordinate pair (x, y) being calculated according to one of the following:
  setting y to a fixed value Y and x to a value in a range of attained dose values at a cumulative volume of Y for the clinical DVH curves in the pairs of DVH curves among the selected subset of pairs DVH curves that are associated with the structure; or
  setting x to a fixed value X and y to a value in a range of attained cumulative volume values at a dose of X for the clinical DVH curves in the pairs of DVH curves among the selected subset of pairs DVH curves that are associated with the structure.

The selected subset of pairs of DVH curves that is selected for a structure of a structure set associated with the at least one planning image may comprise all available pairs of DVH curves, or only some of them. In the latter case, the subset may be determined according to one of the following:
  a subset of pairs of DVH curves where a distance between the protocol DVH curve in the pair of DVH curves and a protocol DVH curve of the current patient is below a set tolerance value, or
  a subset of pairs of DVH curves where a distance between the protocol DVH curve in the pair of DVH curves and a desired DVH curve is greater than or equal to a distance between a protocol DVH curve of the current patient and the desired DVH curve.

The desired DVH curve for a structure normally corresponds to a uniform dose at a prescription dose level if the structure is a target, and to a uniform dose of zero otherwise.

The selected value in the range of attained values for the selected subset of pairs of DVH curves is typically either a generalized mean value, such as the arithmetic mean, quadratic mean, minimum, or maximum; or a percentile value, such as the median.

To simplify the training step, each DVH curve in the selected subset of pairs of DVH curves may be simplified by a mapping of each curve to a space of reduced dimension by application of a feature extraction method, such as
  a linear decomposition method, such as principal component analysis or singular value decomposition;
  a nonlinear manifold learning method; or
  curve fitting of some form of basis functions, such as Gaussian functions or polynomial functions.

The functional relationship from protocol DVH to estimated clinical DVH may be based on a regression model, the regression model being generated by application of a machine learning algorithm on the selected subset of pairs of DVH curves, or the simplified set of such curve pairs obtained by feature extraction.

The prediction model may be calculated in one go, based on a number of DVH curve pairs provided at the same time, or may be refined over time by updating the sets of patient data for previous patients and re-training the prediction model.

An embodiment also relates to a computer program product comprising computer-readable code means which, when run in a computer will cause the computer to perform the method according to any of the above embodiments, and to a computer system comprising a processor for executing computer programs and program memory holding such a computer program product. The computer program product may comprise a non-transitory storage medium having the code means stored thereon. The embodiment also relates to a treatment planning system for calculating radiation therapy treatment plans, comprising a computer system according to the above.

BRIEF DESCRIPTION OF THE DRAWINGS

The invention will be described in more detail in the following, by way of example and with reference to the appended drawings, in which.

DEFINITIONS

In this document, the following concepts are used:
Plan generation protocol: A plan generation protocol is a procedure for generating a treatment plan based on a given set of patient data, such as imaging data and associated structure sets. A plan generation protocol comprises a number of treatment planning tasks that are to be executed in sequence. Preferably, all steps of a plan generation protocol should be possible to perform in fully automated fashion. The plan generation protocol takes into account the treatment apparatus to be used and the desired dose to different parts of the patient. A plan generation protocol may be a simplified procedure that does not incorporate any information about tradeoffs between different treatment planning aims, such as priorities for sparing of different organs at risk, the protocol thus being configured to generate a treatment plan that reflects the physical limitations of the delivery method but not any clinical decision making. The optimization formulation of a plan generation protocol may, for example, be to minimize the integral dose to the patient subject to a constraint on a sufficient dose to each target structure, or to maximize the uniformity of the target dose and the conformity of the dose to the targets. The plan generation protocol may also incorporate priority information regarding different planning aims, such as priorities for different organs at risk that are to be spared form irradiation, the protocol thus being configured to generate treatment plans that would be clinically acceptable for treatment.

Protocol treatment plan: A protocol treatment plan, sometimes referred to as a protocol plan in this document, is a treatment plan generated by application of a plan generation protocol on a set of patient data.

Protocol DVH is the DVH associated with the dose distribution of the protocol treatment plan. A protocol DVH for a given patient image and structure set comprises one or more protocol DVH curves, each protocol DVH curve being a DVH curve associated with a structure of the structure set and a dose distribution of a protocol plan calculated on the planning image.

DETAILED DESCRIPTION

Figure 1:
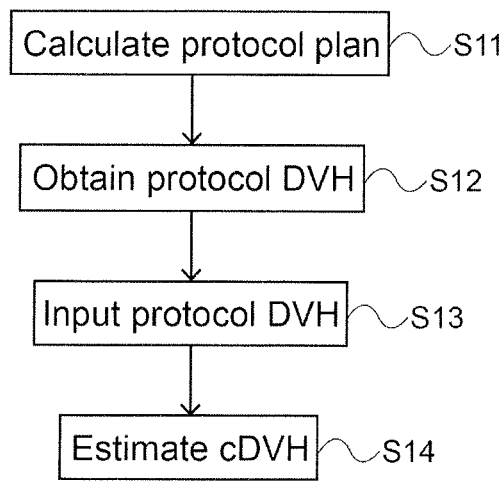
FIG. 1 is a flow chart of an embodiment of the method applied to obtaining a prediction of an achievable DVH for a current patient.

FIG. 1 shows a flow chart outlining an embodiment of a first method according to the invention, for determining planning parameters for a current patient.

In a first step S11, a protocol plan is generated for a current patient by application of a plan generation protocol to patient data, such as a patient image.

In step S12, the protocol DVH curves associated with the dose distribution of the protocol plan are obtained, based on the protocol plan.

In step S13, the protocol DVH curves are transmitted as a query to a prediction model that is trained to map protocol DVH curves to estimates of clinical DVH (cDVH) curves. A method of training such a prediction model will be discussed in connection with FIG. 2.

In step S14, the prediction model is used to obtain an estimate of the clinical DVH curves on the basis of the protocol DVH curves obtained in step S13. These estimated clinical DVH curves may be outputted to a user interface, and/or transmitted as inputs to an automated plan generation method that attempts to recreate the DVH estimate in a treatment plan to be used for the treatment of the current patient.

Figure 2:
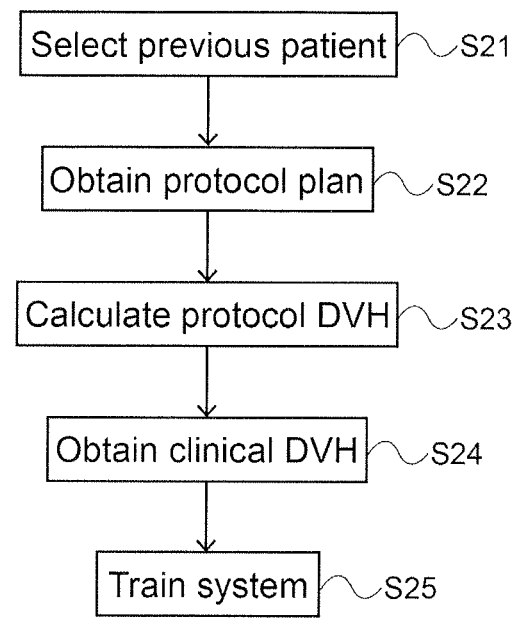
FIG. 2 is a flow chart of an embodiment of the method of creating a prediction model that can be queried for achievable DVHs bases on a library of previously treated patients in the method of FIG. 1.

FIG. 2 discloses an embodiment of a method of training a prediction model to map protocol DVH curves to estimates of clinical DVH curves, creating a prediction model for use, for example, with the method outlined in FIG. 1. The prediction model may be created in one go, considering data from a collection of a number of earlier patients at the same time, or may be built over time.

In step S21 a previous patient is selected from the collection of earlier patients, and patient data for this patient are obtained. Patient data comprise planning image data for the patient and preferably an associated structure set for the planning image data. Alternatively, the structure set may be provided later. Typically, the associated clinical dose distribution for the previous patient is also retrieved in this step.

In step S22, a plan generation protocol is applied to the patient data to obtain the protocol plan. The plan generation protocol is preferably applied in a fully automated fashion. The clinical doses of the previous patient may have been calculated earlier, for the purpose of treatment of the previous patient, or they may be calculated for the purpose of training the prediction model.

In step S23, the protocol DVH curves of the previous patient are retrieved based on the protocol plan obtained in step S22.

In step S24, the clinical DVH curves of the previous patient are retrieved. The clinical DVH curves are defined with respect to the corresponding structure set, and may have been calculated earlier, in connection with treatment planning for the previous patient, or may be calculated in connection with the current method. The steps S21-S24 are repeated, or executed in parallel, for a desired number of previous patients.

In step S25, the protocol DVH curves and the clinical DVH curves for all or a subset of previous patients for which protocol DVH and clinical DVH curves have been determined, are used to train a prediction model to map protocol DVH to estimated clinical DVH. Machine learning algorithms may be employed to train a functional relationship from protocol DVH to estimated clinical DVH, using the features extracted from the relationship between protocol DVH and clinical DVH for the previous patients.

To do this, the relationship between protocol DVH and clinical DVH for the previous patients may be simplified to a feature space of manageable size. This may be achieved using some feature extraction technique, such as a principal component analysis (PCA) or a curve fit using a set of basis polynomials. If the pairs of protocol DVH curves and clinical DVH curves for the previous patients are filtered down to a subset of pairs of DVH curves before the training of the prediction model, the subset may, for example, be the pairs of DVH curves where the protocol DVH curves are similar to the corresponding protocol DVH curves for the current patient. This can be determined as a subset of the DVH curve pairs where a distance between the protocol DVH curve in the pair of DVH curves and the protocol DVH curve for the current patient is small, for example below a specified threshold value. Alternatively, the pairs of DVH curves where the protocol DVH curves are more difficult than for the current patient could be selected. More difficult in this context means that the protocol DVH curve of the previous patient has a larger distance to a desired DVH curve than the corresponding protocol DVH curve of the current patient. Alternatively, the subset of pairs of DVH curves used for training may the set of all pairs of DVH curves. A simple way of determining the desired DVH curve would be to set a uniform dose at a prescription level if the structure is a target and a uniform dose of zero if it is not.

Various machine learning algorithms exist. For example, a support vector regression (SVR) model may be used as a machine learning algorithm. Alternatively, no feature extraction is performed, and the prediction model instead configured to generate estimated clinical DVH curves by mapping protocol DVH points to estimated clinical DVH points, the mapping being based on a functional relationship between protocol DVH and clinical DVH for the previous patients. A protocol DVH point $(x_1, y_1)$, with $x_1$ denoting dose and $y_1$ cumulative volume, may be mapped to an estimated clinical DVH point $(x_2, y_2)$ by setting $y_2=y_1$ and then setting $x_2$ to a dose value in the range of attained clinical dose values at a cumulative volume of $y_2$ the for the selected subset of previous patients. The value selected in the range of attained values may be a generalized mean value, such as the arithmetic mean, minimum, or maximum, or a percentile value, such as the median or third quartile value. Alternatively, the point $(x_1, y_1)$ may be mapped to the point $(x_2, y_2)$ by setting $x_2=x_1$ and setting $y_2$ to value based on the attained range of cumulate volumes at a clinical dose of $x_2$ for the selected subset of previous patients.

Optimization functions for radiation therapy treatment planning commonly measure some distance between a desired dose to a structure and the dose to the structure given the current treatment plan. Examples of distance measures are one-sided or two-sided quadratic differences against a constant dose level or differences between a statistical moment of the dose to the structure and a desired value. A number of optimization functions together defines an optimization problem for the current patient that can be solved by mathematical programming techniques, in order to obtain a treatment plan for the current patient. Examples of optimization algorithms that are applicable if the optimization functions are non-linear measures of the planned dose are interior-point methods and sequential quadratic programming methods. Radiation beams with uniform fluence profiles scaled such that the average dose to the targets equals a prescription dose level may be used as an initial point for the optimization process.

Figure 3:
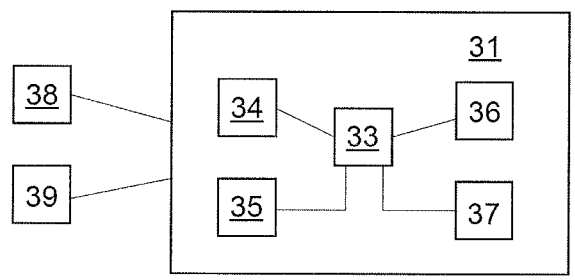
FIG. 3 is an overview of a computer system for performing the method.

FIG. 3 is a schematic representation of a computer system in which the inventive method may be performed. A computer 31 comprises a processor 33, a first and a second data memory 34, 35 and a first and a second program memory 36, 37. Preferably, one or more user input means 38, 39 are also present, in the form of a keyboard, a mouse, a joystick, voice recognition means or any other available user input means. The user input means may also be arranged to receive data from an external memory unit.

The first data memory 34 comprises a number of protocol DVHs for previous patients, a number of corresponding clinical DVHs for the same previous patients and a storage for the calculated relationships between these protocol DVHs and clinical DVHs. The second data memory 35 holds data related to one or more current patients for which treatment plans are to be developed. The first program memory holds a computer program arranged to make the computer perform the method steps discussed in connection with FIG. 1. The second program memory holds a computer program arranged to make the computer perform the method steps discussed in connection with FIG. 2.

As will be understood, the data memories 34, 35 and the program memories are shown and discussed schematically. There may be several data memory units, each holding one or more different types of data, or one data memory holding all data in a suitably structured way, and the same holds for the program memories. For example, there may be separate memories or memory segments for data related to different parts of the body, to facilitate searching for relevant DVH and relationship data for a particular patient, based on the body part that is to be treated. One or more memories may also be stored on other computers. For example, the computer may be arranged to perform only one of the methods, there being another computer for performing the other method.

The invention claimed is:

1. A method for use in radiation therapy treatment planning, comprising:

a. obtaining a protocol plan, which has been created by applying a plan generation protocol to a set of patient data for a current patient, said set of patient data comprising at least one planning image;

b. calculating at least one protocol dose volume histogram (DVH) curve, each protocol DVH curve relating a dose distribution for the protocol plan to a volume of a structure in a structure set, the dose distribution and the structure set being associated with the at least one planning image;

c. obtaining estimated clinical DVH curves by sending the at least one protocol DVH curve as a query to a prediction model, the prediction model being arranged to determine estimated clinical DVH curves on the basis of the at least one protocol DVH curve for the current patient based on a relationship between previous protocol DVH curves and previous clinical DVH curves for a collection of previous patients, wherein the estimated clinical DVH curves are determined based on clinical DVH curves from previous patients that have protocol DVH curves having a distance to the at least one protocol DVH curve of the current patient below a specified threshold value; and d. using at least one of the estimated clinical DVH curves in treatment planning for the current patient.

2. The method according to claim 1, wherein the plan generation protocol is a sequence of tasks to be performed sequentially, the tasks involving at least one of the following tasks:

augmenting the structure set with additional structures, either manually or by automatic image segmentation;
defining radiation beams;
defining settings including resolutions and tolerances;
defining an optimization problem and optimizing a dose with respect to the optimization problem; or
calculating a clinical dose distribution.

3. The method according to claim 2, wherein defining the optimization problem further comprises updating the optimization problem based on the dose distribution for the protocol plan.

4. A computer program product comprising non-transitory computer-readable code means which, when run in a computer will cause the computer to perform the method according to claim 1.

5. A computer system comprising a processor for executing computer programs and program memory holding a computer program product according to claim 4.

6. A treatment planning system for calculating radiation therapy treatment plans, comprising a computer system according to claim 5.

7. A method of training a prediction model for use in radiation therapy treatment planning, the training of the prediction model comprising the following steps:

a. obtaining a set of patient data for a previous patient, the set of patient data comprising at least one planning image;

b. obtaining a plan generation protocol;

c. obtaining a protocol plan of the previous patient by applying the plan generation protocol to the set of patient data;

d. calculating at least one protocol dose volume histogram (DVH) curve for the previous patient, each protocol DVH curve relating a dose distribution for the protocol plan of the previous patient to a volume of a structure in a structure set associated with the at least one planning image;

e. obtaining a clinical DVH curve associated with each protocol DVH curve, each clinical DVH curve relating a clinical dose distribution for the previous patient to the volume;

f. performing steps a-e for each of a number of previous patients to obtain a number of pairs including a protocol DVH curve and an associated clinical DVH curve;

g. selecting a subset of the pairs of DVH curves; and h. training a machine learning model using the pairs of protocol DVH curve and associated clinical DVH curve of the previous patients, the machine learning model being configured to take protocol DVH curves of a current patient as input and return estimated clinical DVH curves as input, the process of training the machine learning model involving adjusting system parameters of the machine learning model toward minimization of a deviation between estimated clinical DVH curves and true clinical DVH curves for the previous patients.

8. The method according to claim 7, wherein the selected subset comprises all DVH pairs.

9. The method according to claim 7, wherein according to a functional relationship between protocol DVH and estimated clinical DVH, the estimated clinical DVH curve is described by a sequence of coordinates pairs (x, y), each coordinate pair (x, y) being calculated according to one of the following:

setting y to a fixed value Y and x to a value in a range of attained dose values at a cumulative volume of Y for the clinical DVH curves in the pairs of DVH curves among the selected subset of pairs of DVH curves that are associated with the structure; or setting x to a fixed value X and y to a value in a range of attained cumulative volume values at a dose of X for the clinical DVH curves in the pairs of DVH curves among the selected subset of pairs of DVH curves that are associated with the structure.

10. The method according to claim 9, wherein the value in the range of attained dose values or the range of attained cumulative volume values for the selected subset of pairs of DVH curves is one of the following:

a generalized mean value, including the arithmetic mean, quadratic mean, minimum, or maximum; or
a percentile value, including the median.

11. The method according to claim 7, wherein the selected subset of pairs of DVH curves is determined as a subset of pairs of DVH curves where a distance between the protocol DVH curve in the pair of DVH curves and a current protocol DVH curve of a current patient is less than or equal to a tolerance value.

12. The method according to claim 7, wherein the selected subset of pairs of DVH curves is determined as a subset of pairs of DVH curves where a distance between the protocol DVH curve in the pair of DVH curves and a desired DVH curve is greater than or equal to a distance between a current protocol DVH curve of the current patient and the desired DVH curve.

13. The method according to claim 12, wherein the desired DVH curve for a structure corresponds to a uniform dose at a prescription dose level if the structure is a target and a uniform dose of zero otherwise.

14. The method according to claim 7, further comprising; the step of simplifying each DVH curve in the selected subset of pairs of DVH curves before defining a functional relationship, by mapping the curve to a space of reduced dimension by application of a feature extraction method, comprising:

a linear decomposition method, including principal component analysis or singular value decomposition;

a nonlinear manifold learning method; or curve fitting of some form of basis functions, including Gaussian functions or polynomial functions.

15. The method according to claim 7 wherein a functional relationship from protocol DVH to estimated clinical DVH is based on a regression model, the regression model being generated by application of a machine learning algorithm on the selected subset of pairs of DVH curves, or a simplified set of such curve pairs obtained by feature extraction.

16. The method according to claim 7, further comprising refining the prediction model over time by updating the set of patient data for previous patients and re-training the prediction model.

* * * * *